US007262010B2

(12) United States Patent
Schaad et al.

(10) Patent No.: US 7,262,010 B2
(45) Date of Patent: Aug. 28, 2007

(54) **REAL-TIME PCR PRIMERS AND PROBES FOR IDENTIFICATION OF *RALSTONIA SOLANACEARUM* RACE 3, BIOVAR 2 IN POTATO AND OTHER PLANTS**

(75) Inventors: Norman W. Schaad, Meyersville, MD (US); Phillip E. Gaush, Charles Town, WV (US); Meric Ozakman, Kucuk Esat (TR)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 10/283,346

(22) Filed: Oct. 30, 2002

(65) Prior Publication Data

US 2004/0086865 A1 May 6, 2004

(51) Int. Cl.
*C12Q 1/68* (2006.01)

(52) U.S. Cl. .......................................................... 435/6

(58) Field of Classification Search .................... 435/6, 435/91.1, 92.1; 536/23.1, 24.1, 24.3, 24.33
See application file for complete search history.

(56) References Cited

OTHER PUBLICATIONS

Stratagene Catalog, 1988.*
Boehringer Mannheim Biochemicals Catalog, 1997.*
Ito et al. Fluorescent differential display: arbitrarily primed RT-PCR fingerprinting on an automated DNA sequencer. 1994. FEBS Letters vol. 351:231-236.*
Roest-Crollius et al. Genebank Accession No. AL234392.*
Genebank accession Nos. AE005991.1, AP008207.1 and AP003045.2 pp. 1-3.*
Genebank accession Nos. AE016814.1, AE005827.1, AF210625.2 and NM_207880.1 pp. 1-3.*
Ciampi, L., et al., "Latent Infection of Potato Tubers by *Pseudomona solanacearum", Am. Potato J.*, vol. 57, pp. 377-386, Jan. 22, 1980.
Fegan, M., et al., "Phylogeny, Diversity and Molecular Diagnostics of *Ralstonia solanacearum", In: Bacterial Wilt Disease: Molecular and Ecological Aspects*, pp. 19-33, 1998.
Fegan, M., et al., "Development of a Diagnostic Test Based on the Polymerase Chain Reaction (PCR) to Identify Strains of *R. solanacearum* Exhibiting the Biovar 2 Genotype", *In: Bacterial Wilt Disease: Molecular and Ecological Aspects*, pp. 34-43, 1998.
Frederick, R., et al., "Identification and Differentiation of *Tilletia indica* and *T. Walkeri* Using the Polymerase Chain Reaction", *Phytopathology*, vol. 90, pp. 951-960, May 22, 2000.
Hayward, A.C., et al., "Round Table on Bacterial Wilt (Brow Rot) of Potato", *In: Bacterial Wilt Disease: Molecular and Ecological Aspects*, pp. 420-429, 1998.
Schaad, N.W., et al., "Real-Time Polymerase Chain Reaction for One-Hour On-Site Diagnosis of Pierce's Disease of Grape in Early Season Asymptomatic Vines", *Phytopathology*, vol. 92, (7), pp. 721-728, 2002.
Schoen, C.D., et al., "Detection of Potato Leafroll Virus in Dormant Potato Tubers by Immunocapture and a Fluorogenic 5' Nuclease RT-PCR Assay", *Phytopathology*, vol. 86, (9), 1996.
Weller, S.A., et al., "Detection of *Ralstonia solanacearum* Strains with a Quantitative Multiplex, Real-Time, Fluorogenic PCR (Taq-Man) Assay", *Applied and Environmental Microbiology*, vol. 66, (7), pp. 2853-2858, Jul. 2000.
Zhang, A.W., et al., "Molecular Detection of *Diaporthe phaseolorum* and *Phomopsis longicolla* from Soybean Seeds", *Phytopathology*, vol. 89, (9), pp. 796-804, 1999.

* cited by examiner

*Primary Examiner*—Jeffrey Fredman
*Assistant Examiner*—Heather G. Calamita
(74) *Attorney, Agent, or Firm*—John D. Fado; Evelyn M. Rabin

(57) ABSTRACT

*Ralstonia solanacearum*, the causal agent of bacterial brown rot of potato, is often carried latently in seed potato tubers. Primers and a probe were designed for a real-time BIO-PCR assay technique for detecting potato tubers latently infected with *R. Solanacearum*. Using naturally infected potato tubers, as few as 20 cells/ml extract could be detected. Two of 14 naturally infected potato tubers with no disease symptoms were positive by the newly described real-time BIO-PCR (pre-enrichment on agar or in liquid medium) assay but not by direct real-time PCR.

6 Claims, 1 Drawing Sheet

GATCTTGTAA GCCTTGGTAC CCAGGTGGTG CCACGCTTCC TTCCCATCGC  50

TGAAGCCAAG GGCGCAGTTC CACACCCGTG ACCTGATAGT TGAAACTGCC 100

CAGCAGGTCG CCATTCCCAT ACAGAATTCG ACCGGCACGC CGAGCCTGAA 150
          *Primer 630*

CCTTGCGCGC GGTGGCCAAA CTCATCTGGG CCATTCTTGC GAAACGACTT 200

GCCTTGCTGC TGCCAAATCG CCGTGCCGAT GGTCAATGGT GACAACGGTT 250

TCCACTTCGT ACCATCCGGC GCCAGCCCTT TGTCATGGCG CTCCTGA<u>TTC</u>  300

<u>ACCGCAAACA GCG</u>A<u>TTCGCC GATGCTTCCC A</u> G<u>CATCTGCTGGGGCGTA</u>AT 350
 Forward Primer    Probe     Reverse Primer

CACTTCCTGG CGCACTGCAC TCAACGCTTG CAGCAGGTGT TCGGCTTGAA 400

ATTCGTAGGC GAATTGCATG TGATTGCCCC GTGGTGATGG AGATGCGCCA 450
     *Primer 631*

GCGAGGCCGC CCACCTATT TCTTGTAGAC CAACCGCCCG ATACGCTGTT 500

TATCGAGGGG CCGCGCGGTC TTCCGGCGCT TCGGTTCCCA TGAACGTGAC 550

ACGCCTGTCC TAGAGCGACC  570

FIG. 1

SEQUENCE LISTING

<160> NUMBER OF SEQ ID NOS: 6

<210> SEQ ID NO 1
<211> LENGTH: 570
<212> TYPE: DNA
<213> ORGANISM: Ralstonia solanacearum

<400> SEQUENCE: 1

| | | | | | | |
|---|---|---|---|---|---|---|
| gatcttgtaa | gccttggtac | ccaggtggtg | ccacgcttcc | ttcccatcgc | tgaagccaag | 60 |
| ggcgcagttc | cacaccgtg | acctgatagt | tgaaactgcc | cagcaggtcg | ccattcccat | 120 |
| acagaattcg | accggcacgc | cgagcctgaa | ccttgcgcgc | ggtggccaaa | ctcatctggg | 180 |
| ccattcttgc | gaaacgactt | gccttgctgc | tgccaaatcg | ccgtgccgat | ggtcaatggt | 240 |
| gacaacggtt | tccacttcgt | accatccggc | gccagcccctt | tgtcatggcg | ctcctgattc | 300 |
| accgcaaaca | gcgattcgcc | gatgcttccc | agcatctgct | ggggcgtaat | cacttcctgg | 360 |
| cgcactgcac | tcaacgcttg | cagcaggtgt | tcggcttgaa | attcgtaggc | gaattgcatg | 420 |
| tgattgcccc | gtggtgatgg | agatgcgcca | gcgaggccgc | cccacctatt | tcttgtagac | 480 |
| caaccgcccg | atacgctgtt | tatcgagggg | ccgcgcggtc | ttccggcgct | tcggttccca | 540 |
| tgaacgtgac | acgcctgtcc | tagagcgacc | | | | 570 |

```
<210> SEQ ID NO 2
<211> LENGTH: 13
<212> TYPE: DNA
<213> ORGANISM: Ralstonia solanacearum

<400> SEQUENCE: 2
accgcaaaca gcg                                                      13

<210> SEQ ID NO 3
<211> LENGTH: 16
<212> TYPE: DNA
<213> ORGANISM: Ralstonia solanacearum

<400> SEQUENCE: 3
catctgctgg ggcgta                                                   16

<210> SEQ ID NO 4
<211> LENGTH: 17
<212> TYPE: DNA
<213> ORGANISM: Ralstonia solanacearum

<400> SEQUENCE: 4
ttcgccgatg cttccca                                                  17

<210> SEQ ID NO 5
<211> LENGTH: 21
<212> TYPE: DNA
<213> ORGANISM: Ralstonia solanacearum

<400> SEQUENCE: 5
atacagaatt cgaccggcac g                                             21

<210> SEQ ID NO 6
<211> LENGTH: 22
<212> TYPE: DNA
<213> ORGANISM: Ralstonia solanacearum

<400> SEQUENCE: 6
cgtaggcgaa ttgcatgtga tt                                            22
```

REAL-TIME PCR PRIMERS AND PROBES FOR IDENTIFICATION OF *RALSTONIA SOLANACEARUM* RACE 3, BIOVAR 2 IN POTATO AND OTHER PLANTS

BACKGROUND OF THE INVENTION

1. Field of the Invention

Brown rot of potato is caused by *Ralstonia solanacearum* race 3 biovar (bv) 2. This invention relates to novel PCR primers and the development of real-time PCR assays for the rapid detection of the potato brown rot pathogen *R. Solanacearum* race 3 bv 2.

2. Description of the Relevant Art

*Ralstonia solanacearum*, the causal agent of bacterial wilt, infects over 100 plant species (Kelman, A. 1953. *North Carolina Agric. Exp. Stn. Tech. Bull.* No. 99). The species has been subclassified into races and biovars. *R. Solanacearum* race 3 bv 2 is a strain that has become adapted to temperate climates (Haywood et al. 1998. In: *Bacterial Wilt Disease: Molecular and Ecological Aspects*, Prior et al., Eds. Springer Verlag, Berlin, Germany; Stead et al. 1996. In: *Conference Proceedings—Brighton Crop Protection Conference—Pests and Diseases* 1996, British Crop Protection Council, Farnham, Surrey, United Kingdom, Pages 1145–1152). Other biovars of *R. solanacearum* can infect potatoes; however, bv 2 is by far the most destructive biovar in temperate areas. The organism has a narrow host range primarily infecting potato (Hayward, A. C. 2000. *Ralstonia solanacearum*. Encyclopedia of Microbiology, Vol. 4, Second Edition, Academic Press, New York, N.Y.). Brown rot has emerged recently as a serious disease of potato in Western Europe (Stead et al., supra) and *R. Solanacearum* bv 2 is listed as a zero tolerance quarantine organism in the European Union (EU) (1998. *Official J. Eur. Communities* L-235: 1–39). In those countries affected by brown rot, the costs of disease surveillance and eradication have become considerable. The pathogen has been reported in potato in Turkey; but it has not yet been observed in potato in the continental U.S. where no regulation in potato currently exists. However, the report of finding bv 2 in geranium in Wisconsin (Williamson et al. 2001. *Phytopathology* 91: S75) and Pennsylvania (Kim et al. 2002. *Phytopathology.* 92:S42) could result in movement of the pathogen into potato.

Asymptomatic seed potato tubers, i.e., those having latent infections, are a major factor in the dissemination of *R. Solanacearum* to new production fields in Europe (Ciampi et al. 1980. *Am. Potato J.* 57: 377–386). Because pathogen-free seeds are very important for controlling the disease, assays for detecting *R. Solanacearum* must be very sensitive. In the EU, seed potato tubers must be certified to be free of *R. solanacearum* using a recommended serological or classical polymerase chain reaction (PCR)-based technique (*Official J. Eur. Communities*, supra). Sensitivity of the serological (Elphinstone et al. 1996. *OEPP/EPPO Bull.* 26: 663–678) and PCR (Seal et al. 1993. *J. Gen. Microbiol.* 139: 1587–1594) techniques are similar ranging from $10^3$–$10^4$ cfu/ml in water or potato core tissue extracts spiked with cells of *R. solanacearum*. The specificity of the classical PCR technique is very high using primers designed from a DNA fragment described by Fegan et al. (1998. In: *Bacterial Wilt Disease: Molecular and Ecological Aspects*, Prior et al., Eds., Springer-Verlag, Berlin, Germany); however, costs of classical PCR is much greater than real-time PCR due to the need to do a Southern blot analysis to confirm identification of the PCR product (Schaad et al. 1999. *Plant Dis.* 83: 1095–1100). A real-time PCR assay has been described for the detection of *R. solanacearum* race 3 bv 2; however, infected tubers were not tested and the sensitivity of the assay was relatively low (Weller et al. 2000. *Appl. Environ. Micro.* 66 (7): 2853–2858).

*R. solanacearum* can be considered a major economic threat to United States agriculture; therefore, there exists a need for new technologies to be examined and novel methods to be developed for the detection and identification of the pathogen causing brown rot in potato. If *R. solanacearum* bv 2 were introduced into potato, all potato shipments would be stopped, resulting in major economic losses. Thus, specific primers and methods capable of identifying latent infections of *R. solanacearum* race 3 bv 2 in seed potato tubers rapidly and economically are needed.

SUMMARY OF THE INVENTION

We have discovered a highly sensitive real-time BIO-PCR technique using oligonucleotide sequences which are capable of amplifying DNA fragments specific for identifying the pathogen *R. solanacearum* race 3 bv 2 and utilizing the rapid cycling portable Smart Cycler SC (Cepheid, Sunnyvale, Calif.).

In accordance with this discovery, it is an object of the invention to provide the novel oligonucleotides for use as primers for PCR assays for the specific detection and identification of *R. solanacearum* race 3 bv 2.

It is an added object of the invention to provide a probe for use in the detection of *R. solanacearum* race 3 bv 2 by real-time PCR.

It is another object of the invention to provide PCR assay methods utilizing the novel primers and probe.

It is an another added object of the invention to provide a kit for use in the detection of *R. solanacearum* race 3 bv 2.

Other objects and advantages of the invention will become readily apparent from the following description.

BRIEF DESCRIPTION OF THE DRAWINGS

FIG. 1 shows the nucleotide sequence of the cloned 570 bp DNA fragment (SEQ ID NO:1) of *R. solanacearum* (Fegan et al., supra). The sequences of the primers and probe of the invention: Forward primer RSC-F (SEQ ID NO:2), Reverse primer RSC-R (SEQ ID NO:3), and the probe RSC-P (SEQ ID NO:4) are in bold type and underlined. Primers 630 (forward, SEQ ID NO:5) and 631 (reverse; SEQ ID NO:6) of Fegan et al. are in bold type.

DETAILED DESCRIPTION OF THE INVENTION

Classical polymerase chain reaction (PCR) methods have been described for the identification and detection of numerous plant pathogens (Henson et al. 1993. *Ann. Rev. Pytopath.* 31: 81–109). Moreover, several real-time fluorescent PCR assays have been developed recently for bacterial (Schaad et al. 1999, supra), viral (Roberts et al. 2000. *J. Virol. Methods* 88: 1–8; Schoen et al. 1996. *Phytopathology* 86: 993–999), and fungal (Bohm et al. 1999. *J. Phytopathology* 147: 409–416; Frederick et al. 2000. *Phytopathology* 90: 951–960; Zhang et al. 1999. *Phytopathology* 89:796–804) plant pathogens. Real-time PCR has several advantages compared to classical PCR. First, it combines the sensitivity of PCR along with the specificity of nucleic acid hybridization. Second, there is no need for agarose gels and the subsequent Southern blot hybridization steps that are necessary to confirm the identity of PCR products in classical PCR assays. Third, up to four different fluorescent dyes can be incorporated in a single reaction that allows for multiplexed reactions using different probes for either the same or different pathogens. Finally, many samples can be assayed simultaneously (up to 96 using the ABI Prism 7700 Sequence Detection System), and the assays can be completed within 2–3 hr. Recently, a portable analytical thermal cycling instrument, the Smart Cycler® (Cepheid, Inc., Sunnyvale, Calif.), was introduced for conducting real-time PCR directly in the field (Belgrader et al., 2001. *Anal. Chem.* 73: 286–289; Belgrader et al. 1999. *Science* 284: 449–450). This would negate the requirement for sending samples to the laboratory for analysis and thus would result in significantly more rapid diagnoses.

The invention provides for novel PCR assays for the identification of the pathogen *R. solanacearum* race 3 bv 2. The real-time fluorescent PCR assays are robust, rapid, and allow for high sample throughput (up to 96 samples at one time on a 7700 Sequence Detection System, or for more rapid results, a portable Smart Cycler). The newly described real-time primers and probes designed from published sequences (Fegan et al., supra) were highly specific to *R. solanacearum* bv 2. No strains of any other biovar of *R. solanacearum* reacted with the primers; nor did any other bacteria tested. These results indicate that the chosen sequences are unique to *R. solanacearum* (Fegan et al. and Weller et al., supra). In addition, real-time PCR can be combined with BIO-PCR in order to achieve still further sensitivity.

The BIO-PCR method, disclosed in U.S. Pat. No. 6,410,223, herein incorporated by reference, combines biological preamplification of the PCR target organism with enzymatic amplification of the PCR target. Briefly, the advantages of the BIO-PCR method, over those of the standard PCR assay, include the detection of live cells only, a 100–1000 fold increase in sensitivity, and elimination of PCR inhibitors associated with plant samples thereby eliminating false negatives. Sample processing can be further simplified by directly processing the samples comprising the expanded cells without further DNA extraction. However, even if a DNA extraction step is included, an advantage of the BIO-PCR methodology is that the DNA is extracted from a growing, viable population of cells or microorganisms. The enhanced sensitivity of the BIO-PCR method is particularly valuable, for example, in those screening situations where the monetary value of a particular seed type is high, and thus it is desirable to test the smallest quantity of seeds possible, and where among trading partners, there is zero tolerance or quarantine for contaminating pathogens.

The preamplification enrichment step involves a plating step on an agar growth medium (or a liquid medium) prior to PCR analysis. A single cell per 0.1 ml can be detected because the single cell multiplies into a colony containing over 1000 cells on the agar medium. Bacteria are recovered from suspect seed potatoes by extracting core tissue from 200 tubers. Aliquots of 0.1 ml of the extracts are pipetted onto mSMSA agar medium; plates are incubated at 28° C. For BIO-PCR, each of five plates is washed one to three times with 1.0 ml of water and 1 µl of the resulting 5–15 ml of wash solution can be used for direct PCR-amplification with or without further DNA extraction or sample processing. Similarly, for standard PCR, either the DNA can be extracted or intact cells used. Since only pinpoint-size colonies are needed, incubation time ranges from only 10–15 hr for fast growing bacteria, such as *R. solanacearum*, to 24–48 hrs for most plant pathogenic bacteria, depending on the media. Since the incubation time is short, few other bacterial colonies are present.

Real-time BIO-PCR utilizing a portable Smart Cycler protocol is highly sensitive and useful for detecting bv 2 strains of *R. solanacearum* in seed potatoes which showed no disease symptoms of any kind, i.e., asymptomatic seed potatoes. Detection of as few as 20 cells/ml in potato extract diluted 1:100 indicates that the real-time BIO-PCR technique is highly sensitive and useful for quarantine and certification seed assays. With the BIO-PCR protocol, no PCR inhibition was observed. Others have shown that *R. solanacearum* can be detected in spiked potato tuber extracts with PCR, but this is the first time that the organism has been detected in naturally infected asymptomatic tubers using PCR.

The newly introduced Smart Cycler has several advantages, including extremely fast run time, multiple wells for optimization, and portability. A run time of only 20 min has been reported for on-site diagnosis of watermelon fruit blotch using real-time PCR and the Smart Cycler (Schaad et al. 2001. *APS Congress,* 2001). With direct PCR, watermelon fruit blotch or the Pierce's disease bacterium (Schaad et al. 2002. *Phytopathology* 92: 721–728) can be diagnosed in one h or less, including sampling time. A direct assay for brown rot could be completed in 1–2 h; however, direct PCR is considerably less sensitive than BIO-PCR. An important requirement for an assay protocol for seed potatoes is that completion of the assay require only a short time. However, when the role of latently infected tubers in dissemination of *R. solanacearum* is considered, sensitivity is more important than time. Furthermore, where time is very important, direct PCR and BIO-PCR could be conducted simultaneously. In those situations where results are positive for direct PCR, BIO-PCR could then be halted. In addition, if a culture of the organism is desired, cultures set up as for BIO-PCR-could be used for isolation of *R. solanacearum* from asymptomatic tubers. Use of modified SMSA (mSMSA) medium is very reliable, however, 3–4 days are required for isolating the organism. Serological tests such as IFAS (immunofluorescent antibody staining) are widely used, but the level of sensitivity is not higher than $10^4$ cells/ml (Elphinstone et al., supra). Serological tests have an additional disadvantage of detecting dead cells and therefore often result in false positives (Janse, J. D. 1988. *OEPP/EPPO Bull.* 18: 343–351).

Our results of direct real-time PCR using extracts spiked with *R. solanacearum* agrees with a reported threshold of $10^2$–$10^4$ cells/ml for classical PCR (Elphinstone et al., supra; Schaad et al. 1995. *Phytopathology* 85: 243–248). Although presumptive results are available in the same day, additional analysis for confirmation of amplified product such as Southern blot is required for classical PCR (Schaad et al. 1999, supra). Weller et al (supra) also designed bv 2-specific real-time primers and probe from the sequence information of Fegan et al (supra). Their system was able to detect $10^4$ cells/ml of bacteria in potato extract. Although our PCR primers and probe were selected from the same sequence information, the nucleotide sequences were completely different form any published sequence and our real-time primers and probe are 10 times more sensitive.

Real-time PCR does not require additional analysis for confirmation of the product (Schaad et al. 1999, supra). In our technique, results of moderately infected tubers are available the same day using direct PCR. Although BIO-PCR requires a second day (24 h to enrich), the ability to detect latent infected tubers is a great advantage for assaying seed potatoes.

The use of the BIO-PCR technique for sensitive detection of bacteria has several advantages over classical PCR including (1) elimination of PCR inhibitors, (2) reducing the chance of a false positive due to dead cells or free DNA, and (3) significant increase in sensitivity due to enrichment of the target cells (Schaad et al. 1995, supra). Our real-time BIO-PCR assay using enrichment in liquid MSMSA medium was equally sensitive to the liquid classical nested BIO-PCR technique (Elphinstone et al., supra). However, that enrichment technique required an extra 48 h and was only tested with spiked tuber extracts. No naturally infected tubers were tested. The need for only 24 h incubation of *R. solanacearum* on mSMSA to result in pinpoint size colonies is considerably faster than BIO-PCR techniques reported for other plant pathogenic bacteria (Schaad et al. 1995, supra). Because the described real-time BIO-PCR assay provides for high sensitivity for detecting *R. solanacearum* bv 2 in asymptomatic potato tubers, the assay should be especially well suitable for quarantine and seed certification programs.

A primer is preferably about sixteen to twenty-four nucleotides long. Primers can hybridize to a DNA strand with the coding sequence of a target sequence and are designated sense primers. Primers can also hybridize to a DNA strand that is the complement of the coding sequence of a target sequence; such primers are designated anti-sense primers. Primers that hybridize to each strand of DNA in the same location or to one another are known as complements of one another. Primers can also be designed to hybridize to a mRNA sequence complementary to a target DNA sequence and are useful in reverse transcriptase PCR.

The primers of the invention can be used for evaluating and monitoring the efficacy of any treatments utilized to eliminate the pathogenic *R. solanacearum*. The primers of the invention can be used to form classical probes and also real-time probes (when fluorescent tags are added).

In brief, the DNA amplification products can be detected by (a) providing a biological sample comprising extracted DNA; (b) amplifying a target sequence of the DNA to provide DNA amplification products carrying a selected target DNA sequence; and (c) detecting the presence of *R. solanacearum* by detecting the presence of the DNA amplification products.

The biological sample may either be bacteria cells or extracted genomic DNA. The biological sample may be a test sample containing DNA extracted from infected plant tissue. The biological sample may be a test sample suspected of containing bacterial cells, and thus the DNA of the bacterial cells, or a test sample containing extracted DNA.

The enzymatic amplification of the DNA sequence is by polymerase chain reaction (PCR), as described in U.S. Pat. No. 4,683,202 to Mullis, herein incorporated by reference. In brief, the DNA sequence is amplified by reaction with at least one oligonucleotide primer or pair of oligonucleotide primers that hybridize to the target sequence or a flanking sequence of the target sequence and a DNA polymerase to extend the primer(s) to amplify the target sequence. The amplification cycle is repeated to increase the concentration of the target DNA sequence. Amplified products are optionally separated by methods such as agarose gel electrophoresis. The amplified products can be detected by either staining with ethidium bromide or by hybridization to a probe sequence. In an alternative embodiment, a probe that hybridizes to the amplified products is labeled either with a biotin moiety and/or at least one probe is labeled with a fluorescently-labeled chromophore. The hybrids are then bound to a solid support such as a bead, multiwell plate, dipstick or the like that is coated with streptavidin. The presence of bound hybrids can be detected using an antibody to the fluorescent tag conjugated to horseradish peroxidase. The enzymatic activity of horseradish peroxidase can be detected with a colored, luminescent or fluorimetric substrate. Conversion of the substrate to product can be used to detect and/or measure the presence of *R. solanacearum* PCR products.

Other methods of PCR using various combination of primers including a single primer to about three primers are known to those of skill in the art and are described in Maniatis (1989. *Molecular Cloning: A Laboratory Manual*. Cold Spring Harbor, N.Y.). Those methods include asymmetric PCR, PCR using mismatched or degenerate primers, reverse transcriptase PCR, arbitrarily primed PCR (Welsh et al. 1990. *Nucleic Acids Res*. 18: 7213–7218), or RAPD PCR, IMS-PCR (Islam et al. 1992. *J. Clin. Micro*. 30: 2801–2806), multiwell PCR (ELOSA) (Luneberg et al. 1993. *J. Clin. Micro*. 31: 1088–1094), and Katz et al. 1993. *Am. J. Vet. Res*. 54: 2021–2026). The methods also include amplification using a single primer as described by Judd et al. 1993. *Appl. Env. Microbiol*. 59:1702–1708).

An oligonucleotide primer sequence must be homologous to a sequence flanking one end of the DNA sequence to be amplified. A pair of oligonucleotide primers, each of which has a different DNA sequence and hybridizes to sequences that flank either end of the target DNA sequence in order for amplification to occur. Design of primers and their characteristics have been described previously. The preferred DNA sequence of the oligonucleotide primer is forward primer 5'-TTCACCGCAAACAGCG-3' (SEQ ID NO:2), reverse primer 5'-TACGCCCCAGCAGATG-3' (SEQ ID NO:3), or complements thereof, or mixtures thereof. (SEQ ID NO:3 as disclosed here and in the Sequence Listing is complementary to the reverse orientation of the bold underlined sequence of FIG. 1.) The primers may also be degenerate primers that hybridize to the target DNA sequence under hybridization conditions for a primer of that size and sequence complementarity.

For the binding and amplification, the biological sample (bacterial cells or extracted DNA) is provided in an aqueous buffer formulated with an effective amount of a divalent cation which is preferable $MgCl_2$, preferably at a concentration of about 0.05–5 mM; an effective amount of DNA polymerase as for example Taq DNA polymerase in the form of native purified enzyme or a synthesized form such as AMPLITAQ (Perkin-Elmer), an effective amount of dNTPs as a nucleotide source, including, dATP, dCTP, dGTP, and dTTP, preferably in a saturating concentration, preferably about 200 μM per dNTP; and an effective amount of one or a pair of oligonucleotide primers. The reaction mixture containing the annealed primer(s) is reacted with a DNA polymerase at about 72° C. to about 94° C. for about 1–10 minutes, to extend the primers to make a complementary strand of the target gene sequence. The cycle is then repeated by denaturing the DNA strands with heat, annealing and extending, preferably for about 25–40 cycles, preferably about 30 cycles.

If designed properly, a single product results. This product is preferably about 450–550-kb in size, whose termini are defined by the oligonucleotide primer(s), and whose length is defined by the distance between the two primers or the length of time of the amplification reaction. The gene sequence then serves as a template for the next amplification cycle.

The amplified DNA product is optionally separated from the reaction mixture and then analyzed. The amplified gene sequence may be visualized, for example, by electrophoresis in an agarose or polyacrylamide gel or by other like techniques, known and used in the art.

The amplified gene sequence may be directly or indirectly labeled by incorporation of an appropriate visualizing label, as for example, a radioactive, calorimetric, fluorometric or luminescent signal, or the like. In addition, the gel may be stained during or after electrophoresis with a visualizing dye such as ethidium bromide or syber green stain wherein the resulting bands by be visualized under ultraviolet light.

In classical PCR, to conclusively prove the identity of the amplified DNA product, a Southern blot assay should be conducted. The amplified products are separated by electrophoresis on a polyacrylamide or agarose gel, transferred to a membrane such as a nitrocellulose or nylon membrane, and reacted with a labeled oligonucleotide probe. The amplified products may also be detected by reverse blotting hybridization (dot blot) in which an oligonucleotide probe specific to the gene sequence is adhered to a nitrocellulose or polyvinylchloride (PVC) support such as a multi-well plate, and then the sample containing labeled amplified product is added, reacted, washed to remove unbound substance, and a labeled amplified product attached to the probe or the gene sequence imaged by standard methods.

In addition to their use in classical PCR assays, the preferred method of amplifying the DNA sequences of *R. solanacearum* is to use the *R. solanacearum*-specific PCR primers with an internal 5'-FAM-labeled oligonucleotide probe sequence in a 5'-fluorogenic real-time TaqMan PCR assay. In most 5'-fluorogenic TaqMan PCR assays, the flanking PCR primers are the same, and the internal fluorescent-labeled probe is designed to be characteristic for a specific sequence (Livak et al. 1995. *PCR Meth. Applic.* 4: 357–362). However, beacons, other than TaqMan, may also be used. In addition, other primers of about sixteen to twenty-four nucleotides in length which specifically hybridize to a target region of SEQ ID NO:1, or the complement of SEQ ID NO:1, will identify *R. solanacearum* provided that (1) such primers are chosen such that the target region flanked by the primers is such that the amplification products can be detected and quantitated by real-time PCR analysis and (2) at least one of the primers comprises SEQ ID NO:2 or SEQ ID NO:3.

An internal oligonucleotide, a 17-mer probe, was labeled with the chromophore FAM: 5'-FAM-TTCGCCGATGCT-TCCCA-TAMRA-3' (SEQ ID NO:4). Additional probes can be made comprising a detectable label conjugated to an oligonucleotide of about fifteen to thirty nucleotides that specifically hybridize to a portion of the SEQ ID NO:1.

The real-time detection assays offer several advantages over the classical PCR assays developed for *R. solanacearum*. First, the real-time assays combine the sensitivity of PCR along with hybridization of the internal oligonucleotide sequence that is present in a *R. solanacearum* sequence. Following PCR, samples do not have to be separated on agarose gels, and the subsequent Southern blots and hybridization steps that are necessary to verify the identity of the PCR products is eliminated. These additional post-PCR confirmation steps can easily add several days for an accurate identification. Also, real-time assays are quantitative. Using the high through put 7700 Sequence Detection system (Applied Biosystems), the *R. solanacearum*-specific 5'-fluorogenic assays are completed within 5 hr. The methodology involved in the assay process makes possible the handling of large numbers of samples efficiently and without cross-contamination and is therefore adaptable for robotic sampling. As a result, large numbers of test samples can be processed in a very short period of time using the 7700 system. Time is a very important factor when eradication procedures are being considered or when trade issues are involved. By using the Smart Cycler, the assay can be completed in one hour or less. Another advantage of real-time PCR is the potential for multiplexing. Since different fluorescent reporter dyes, as for example FAM and VIC®, can be used to construct probes, several different pathogen systems could be combined in the same PCR reaction, thereby reducing the labor costs that would be incurred if each of the tests were performed individually. The advantages of rapid, conclusive data together with labor and cost efficiency make real-time detection systems utilizing the specific primers of the invention a highly beneficial system for monitoring seed and tuber pathogens, especially in those circumstances where seed screening results have major commercial and trade consequences.

The primers and amplification method can further be useful for evaluating and monitoring the efficacy of any treatments utilized to control the spread of *R. solanacearum*.

Similarly, the novel primers and real-time PCR methods are very useful for epidemiology and host-pathogen studies as the primers represent a valuable tools for monitoring natural disease spread, tracking specific seedborne bacteria in field studies, and detecting the presence of the bacteria in imported seed potato lots entering *R. solanacearum*-free areas.

EXAMPLES

The following examples serve as further description of the invention and methods for practicing the invention. They are not intended as being limiting, rather as providing guidelines on how the invention may be practiced.

Example 1

Source and Growth of Bacterial Strains

Strains of *R. solanacearum* and other bacteria used in this study are listed in Table 1. *R. solanacearum* was grown and maintained on TTC agar medium (Kelman, A. 1954. *Phytopathology* 39: 94–96) at 28° C. Other bacterial strains used to determine the specificity of the primers and probe were grown on medium B or YPGA medium (King et al. 2001. In: *Laboratory Guide for Identification of Plant Pathogenic Bacteria*, Third Edition, Schaad et al., Eds., APS Press. For the BIO-PCR assay, mSMSA agar medium was used for enriching *R. solanacearum* (Englebrecht, M. C. 1994. *Bacterial Wilt Newsletter* 10:3–5.

TABLE 1

Strains of *Ralstonia solanacearum* and other bacteria; results of real-time PCR

| Strain | Source | Origin | Host | Race | BV | PCR |
|---|---|---|---|---|---|---|
| *R. solanacearum* | | | | | | |
| UW-139 (FC-6) | 1 | Costa Rica | Plantain | 2 | 1 | − |
| UW-275 (FC-7) | 1 | Costa Rica | *Jelampodium perfoliatum* | 1 | 1 | − |
| JT-526 (FC-325) | 2 | Reunion Is. | *Pelargonium sp.* | ND | 1 | − |
| JR-65 (FC-326) | 2 | USA | Tomato | ND | 1 | − |
| JS-40 (FC-327) | 2 | Columbia | Potato | ND | 1 | − |
| JS-768 (FC-328) | 2 | Guadeloupe | Potato | ND | 1 | − |
| JS-775 (FC-329) | 2 | Honduras | *Musa sp.* | ND | 1 | − |
| Rso 81-2 (FC-230) | 3 | USA | Tomato | ND | 1 | − |
| Rso 81-5 (FC-231) | 3 | USA | Tomato | ND | 1 | − |
| Rso 84-1 (FC-232) | 3 | USA | Tomato | ND | 1 | − |
| Rso 87-105 (FC-234) | 3 | USA | Tomato | ND | 1 | − |
| Rso 96-41 (FC-235) | 3 | USA | Tomato | ND | 1 | − |
| Ps-102 (ATCC-9910) | 4 | USA | Tobacco | ND | 1 | − |
| Ps-119 | 4 | USA | Potato | ND | 1 | − |
| Ps-120 | 4 | USA | Peanut | ND | 1 | − |
| Ps-121 | 4 | USA | Potato | ND | 1 | − |
| Ps-123 | 4 | USA | Tomato | ND | 1 | − |
| Ps-124 | 4 | USA | Tobacco | ND | 1 | − |
| UW-72 (FC-530) | 1 | Greece | Potato | 3 | 2 | + |
| NL-pot. (FC-510) | 5 | Netherlands | Potato | 3 | 2 | + |
| TR-105 (FC-529) | 6 | Turkey | Potato | 3 | 2 | + |
| UW-276 (FC-533) | 1 | Mexico | Potato | 3 | 2 | + |
| UW-257 (FC-535) | 1 | Costa Rica | Potato | 3 | 2 | + |
| JT-516 | 2 | Reunion Is. | Potato | 3 | 2 | + |
| MB-12 (FC-311) | 7 | Nepal | Potato | 3 | 2 | + |
| MB-9 (FC-310) | 7 | Nepal | Potato | 3 | 2 | + |
| NA-5 (FC-305) | 7 | Nepal | Potato | 3 | 2 | + |
| NF-5 (FC-306) | 7 | Nepal | Potato | 3 | 2 | + |
| BA-4 (FC-309) | 7 | Nepal | Potato | 3 | 2 | + |
| UW-145 (FC-53) | 1 | Australia | Potato | 3 | 2 | + |
| FC-396 | 8 | Guatemala | *Pelargonium sp.* | 3 | 2 | + |
| FC-400 | 8 | Guatemala | *Pelargonium sp.* | 3 | 2 | + |
| FC-410 | 8 | Guatemala | *Pelargonium sp.* | 3 | 2 | + |
| FC-417 | 8 | Guatemala | *Pelargonium sp.* | 3 | 2 | + |
| UW-457 (FC-17) | 1 | Peru | Potato | ND | N2 | − |
| UW-416 (FC-11) | 1 | Australia | *Solanum nigrum* | 1 | 3 | − |
| UW-432 (FC-140) | 1 | Australia | *Zinnia sp.* | 1 | 3 | − |
| UW-434 (FC-15) | 1 | Australia | *S. nigrum* | 1 | 3 | − |
| UW-440 (FC-16) | 1 | Australia | *Streltzia reginae* | 1 | 3 | − |
| P-1 (FC-254) | 7 | Thailand | Pepper | 1 | 3 | − |
| P-2 (FC-255) | 7 | Thailand | Pepper | 1 | 3 | − |
| Pe-UD (FC-256) | 7 | Thailand | Pepper | 1 | 3 | − |
| Pe-BK (FC-257) | 7 | Thailand | Pepper | 1 | 3 | − |
| To-4 (FC-290) | 7 | Thailand | Tomato | 1 | 3 | − |
| Po-1155 | 7 | Thailand | Pepper | 1 | 3 | − |
| Supp-1875 (B2-1) | 2 | Japan | Tobacco | 1 | 3 | − |
| PB 41-2 (FC-296) | 7 | Thailand | *Zingiber officinale* | 1 | 4 | − |
| PB 41-3 (FC-297) | 7 | Thailand | *Z. officinale* | 1 | 4 | − |
| PB 41-1 (FC-295) | 7 | Thailand | *Z. officinale* | 1 | 4 | − |
| Cu-1290 (FC-274) | 7 | Thailand | *Cucuma alismatifolia* | 1 | 4 | − |
| Cu-1291 (FC-275) | 5 | Thailand | *C. alismatifolia* | 1 | 4 | − |
| Cu-1351 (FC-276) | 5 | Thailand | *C. alismatifolia* | 1 | 4 | − |
| Cu-1352 (FC-277) | 5 | Thailand | *C. alismatifolia* | 1 | 4 | − |
| UW-357 | 1 | China | Olive | 1 | 4 | − |
| UW-74 | 1 | Ceylon | Potato | 1 | 4 | − |
| UW-359 | 1 | China | *Z. officinale* | 1 | 4 | − |
| FC-338 | 7 | Japan | *S. melongena* | ND | 4 | − |
| UW-360 | 1 | China | Mulberry | 1 | 4 | − |
| UW-151 | 1 | Australia | Ginger | 1 | 4 | − |
| UW-373 | 1 | China | Mulberry | 1 | 5 | − |
| Blood Disease Bacterium | | | | | | |
| Supp 1723 | 2 | Indonesia | Banana | NA | NA | |

TABLE 1-continued

Strains of *Ralstonia solanacearum* and other bacteria; results of real-time PCR

| Strain | Source | Origin | Host | Race | BV | PCR |
|---|---|---|---|---|---|---|
| *Erwinia atroseptica* | | | | | | |
| Eca-602 | 6 | Turkey | Potato | NA | NA | − |
| Eca-504 | 6 | Turkey | Potato | NA | NA | − |
| *Erwinia carotovora* | | | | | | |
| Ecc-Tub | 6 | Turkey | Potato | NA | NA | − |
| Ecc-604 | 6 | Turkey | Potato | NA | NA | − |
| Ecc-301 | 6 | Turkey | Potato | NA | NA | − |
| *P. fluorescens* | | | | | | |
| ATCC 17559 (FC122) | 9 | USA | Unknown | NA | NA | − |
| ATCC 9446 (FC123) | 9 | USA | Unknown | NA | NA | − |
| ATCC 12985 (FC124) | 9 | USA | Unknown | NA | NA | − |
| *P. marginalis* | | | | | | |
| PM-174 (FC-85) | 4 | USA | Unknown | NA | NA | − |
| *C. m. sepedonicus* | | | | | | |
| CMS-INM (FH-20) | 10 | USA | Potato | NA | NA | − |
| CMS-OFF (FH-22) | 10 | USA | Potato | NA | NA | − |
| *X. campestris* | | | | | | |
| XC-125 (FB-1018) | 4 | USA | Cauliflower | NA | NA | − |
| LMG-523 (FB-1021) | 11 | Burundi | Brassica | NA | NA | − |

Source: 1, C. Allen, Wisconsin; 2, Y. Takikawa, Japan; 3, R. Gitaitis, Georgia; 4, N. W. Schaad, International Collection of Phytopathogenic Bacteria; 5, J. D. Janse (diseased tuber), The Netherlands; 6, Meric Ozakman, Turkey; 7, N. Thaveechai, Thailand; 8, S. Kim, Pennsylvania; 9, J. Loper, Oregon; 10, T. German, Wisconsin; 11, M. Lemattre, France. Abbreviations: ND, not determined; NA, not appropriate; ATCC, American Type Culture Collection.

Example 2

Design and Selection of Real-Time PCR Primers and Probe

Real-time primers and probe specific to *R. solanacearum* bv 2 were designed from bv 2-specific sequences (Fegan et al., supra) using Primer Express version 1.0 (Perkin Elmer Applied Biosystems, Foster City, Calif.). The probe is labeled at the 5' terminal nucleotide with the FAM reporter dye and 3' terminal nucleotide with the TAMRA quencher dye. The PCR mixture for each reaction consisted of the following: 1×PCR buffer; 5 mM MgCl$_2$, 200 mM of each dNTP; 1 µM RSC-F (forward primer); 1 µM RSC-R (reverse primer; 400 nM probe; 0.5 U Taq DNA polymerase (Perkin Elmer Applied Biosystems, Foster City, Calif.); 1×additive reagent containing BSA at 1 mg/ml, Trehalose at 750 nm, and Tween 20 at 1% v/v (Cepheid, Sunnyvale, Calif.); and 1 or 10 µl of sample or cell suspension in 25 µl Cepheid optical tubes. For 1 µl samples, 6.25 µl of water were used whereas no water was used for 10 µl samples. PCR was carried out in a Cepheid SmartCycler SC®, as recommended by the manufacturer. Using one set of primers and probe, amplification conditions were optimized for denaturation and annealing times and temperatures. Additional forward primers were ordered and screened for specificity and sensitivity using the same reverse primer and probe. The final combination was then optimized. Results were recorded as cycle threshold ($C_t$) values. The $C_t$ value is defined as the PCR cycle number at which time the signal (fluorescence) of the probe rises above background.

The following amplification conditions were selected: 2 min denaturation at 95° C. followed by 40 cycles of 5 sec denaturation at 95° C. and 30 sec annealing at 58° C. Of the four forward primers tested in combination with reverse primers RSC-R and probe RSC-P, primer RSC-F had the lowest $C_t$ value (Table 2).

TABLE 2

Comparison of four forward primers in real-time PCR using reverse primer RSC-R, probe RSC-P and genomic DNAS of *R. solanacearum* biovar 2 strain TR-1-5.

| Forward Primers | Reverse Primer | Probe | $C_t$ value* |
|---|---|---|---|
| RSC-F | RSC-R | RSC-P | 18.84 |
| RSM1-F | RSC-R | RSC-P | 26.15 |
| RSM2-F | RSC-R | RSC-P | 32.19 |
| RSM3-F | RSC-R | RSC-P | 27.44 |

*$C_t$ cycle threshold value, using 10 ng/µl DNA

Example 3

Specificity and Sensitivity of Primers

For specificity, 17 strains of *R. solanacearum* bv 2, 18 bv 1, 11 bv 3,13 bv 4, one bv 5, the closely related blood disease bacterium (BDB), 11 other bacteria associated with potato, and two xanthomonads were grown on agar media for 48 h. After washing the cells from the plates and diluting 1:100 in sterile MQ water to adjust the concentration to approximately $10^7$ cells/ml, 1.0 ml samples were stored in microfuge tubes at −20° C.

For cell sensitivity, *R. solanacearum* bv 2 strain TR-105 was grown on TTC medium at 28° C. for 24 h. The cells were washed from the plate in sterile MQ water and the suspension adjusted to an OD of 0.1 at 600 nm using a SmartSpec 3000 spectro-photometer (BioRad Inc.). Such suspensions contained approximately $10^8$ cfu/ml. Actual cell concentrations were determined by preparing a 10 fold dilution to $10^{-9}$. One hundred μl of the $10^{-6}$, $10^{-7}$, $10^{-8}$, and $10^{-9}$ dilutions were then plated onto each of three plates of TTC agar medium. After 48 hr the colonies were counted and recorded. One ml of the remaining dilutions was boiled for 10 min and stored at $-20°$ C. for PCR.

For DNA sensitivity, strain TR-105 was grown in 5 ml of nutrient broth (NB) medium at 28° C. for 24 hr and cells harvested by centrifugation at 14,000 rpm for 3 min. After washing the cells three times in sterile saline (0.85% NaCl) solution, DNA was extracted using Puregene Easy DNA extraction kit (Gentra Systems, Minneapolis, Minn.) according to the manufacturer. The concentration of the DNA was measured with a Smartspec 3000, adjusted to 10 ng/μl in sterile MQ water, and ten-fold dilutions made down to 100 fg/μl in sterile MQ water. Biovar 2-specific classical primers 630F and 631R (Fegan et al., supra) were also tested for comparison.

Of the different forward primers tested, primer RSC-F (5'-TTCACCGCAAACAGCG-3'; SEQ ID NO:2) gave the best results with reverse primer RSC-R (5'-TACGCCCCAG CAGATG-3'; SEQ ID NO:3) and probe RSC-P (5'-TTCGC-CGATGCTTCCCA-3'; SEQ ID NO:4) (Table 2). Results of optimization showed that 1 μM of primer concentration provided the lowest $C_t$ value and highest endpoint fluorescence (data not shown).

All bv 2 strains tested resulted in $C_t$ values of 26 or less (Table 1). None of the 43 strains of bvs 1, 3, 4, and 5 or the bv N2 strain produced any fluorescence after 40 cycles. Furthermore, none of the other bacteria, including the closely related BDB, produced any fluorescence (Table 1).

Using DNA and direct PCR, the maximum sensitivity of primers RSC-F and RSC-R and probe RSC-P was 100 fg/μl ($C_t$ value of 35.29). For boiled cells and direct PCR, the threshold was $3.0 \times 10^3$ cfu ($C_t$ value of 38.25; Table 3).

TABLE 3

Sensitivity of real-time PCR of R. solanacearum in water and potato extract with direct PCR and BIO-PCR.

| | Water, Direct | Potato Extract | | |
|---|---|---|---|---|
| | | Direct PCR[c] | BIO-PCR[d] | |
| Cfu/ml[a] | PCR[b] | 1 μl sample | 1 μl sample | 10 μl sample |
| $3.0 \times 10^7$ | 23.67 | 25.31 | 20.27 | ND |
| $3.0 \times 10^6$ | 26.72 | 29.28 | 23.89 | 22.48 |
| $3.0 \times 10^5$ | 29.60 | 32.34 | 27.77 | 24.35 |
| $3.0 \times 10^4$ | 32.85 | 35.27 | 31.14 | 27.91 |
| $3.0 \times 10^3$ | 38.25 | 38.37 | 33.95 | 30.56 |
| $3.0 \times 10^2$ | — | — | 36.38 | 33.29 |
| $3.0 \times 10^1$ | — | — | — | 36.03 |

[a]$OD_{600}$ = 0.1 cell suspension in sterile water was prepared from 24 h old cultures of strain TR-105 grown on TTC agar medium. Ten fold dilutions were made in sterile water. Colony counts determined by counting cfu's on each of three plates after three days at 28° C.;
[b]$C_t$ values of the 10 μl bacterial cell suspensions in water;
[c]Ten μl of spiked potato extracts were boiled for 10 min and 1 μl used directly for PCR;
[d]Spiked potato extracts (100 μl) were spread onto two mSMSA plates and incubated at 28° C. for 24 h. Each plate was washed with 1 ml sterile water and the pooled washings boiled for 10 min.

Example 4

Production of Infected Tubers

Plants of cv Norchip were grown to the flowering stage in sterile potting soil in sterile 20 cm pots in a growth chamber in a BSL-3P containment facility with a 12 h day/night cycle at 23° C. and 12° C., respectively. Using a liquid NB culture of bv 2 strain TR-105 adjusted to 0.1 OD at 600 nm and diluted to $10^{-3}$, 10 ml were poured onto the soil surface of each pot. After growing for 30–40 days under the same conditions as above, plants with wilting symptoms were removed and all resulting tubers harvested, washed, dried, and stored in paper bags at 10° C.

Example 5

Extracting Potato Tubers

Potato tuber extracts were obtained according to official EU methods (Official J. Eur. Communities, supra). Briefly, core tissue was removed from the stem-end of each tuber aseptically and placed into a flask containing 25 ml of 50 mM, pH 7.2 phosphate buffer. After shaking for 4 h at room temperature, the suspension was centrifuged at 10,000×g for 10 min at 4° C. and suspended in 1 ml 10 mM, pH 7.2 phosphate buffer.

Example 6

Assay of Spiked Tuber Extracts

The following protocol was used to assay potato tubers. Core tissue from 200 tubers was extracted and a 1 ml sample was retained. One hundred μl of extract was plated onto each of 5 plates of mSMSA agar medium; plates were incubated at 28° C. Another 100 μl aliquot of extract was boiled for 10 min in a microfuge tube. A classical direct real-time PCR was performed using duplicate samples of 10 μl of extract. If the results of the classical PCR is negative, wash 3 mSMSA plates after 24 h incubation and use 10 μl of wash for BIO-PCR. After 3 days, observe mSMSA for possible colonies of R. solanacearum.

To spike extracts with R. solanacearum, strain TR-105 was grown and diluted 10 fold to $10^{-8}$, as above. One hundred μl of bacterial suspension of each dilution ($10^8$ to $10^{-1}$) was then added to 900 μl of potato core tissue extracts. To determine the actual cfu R. solanacearum/ml, 100 μl of dilutions $10^{-5}$, $10^{-6}$, and $10^{-7}$ were spread onto each of three plates of mSMSA medium using an L shaped glass rod and incubated at 28° C. At the same time 100 μl of each of the dilutions were spread onto five plates of mSMSA for BIO-PCR assay. The remaining 300 μl of each dilution were boiled for 10 min, as above, and stored at $-20°$ C. for direct PCR (no DNA extraction). As a positive control to recognize colonies of R. solanacearum, a culture was streaked onto mSMSA medium and incubated at 28° C. After 24 h incubation, the resulting pinpoint sized colonies of R. solanacearum on each of three plates of mSMSA were washed with 1 ml of sterile water and pooled into one sample and boiled for 10 min. The remaining original potato extract was boiled for 10 min in a microfuge tube and immediately put on ice to use for direct PCR. The other two plates were maintained at 28° C. for five days for visual recovery of R. solanacearum.

The threshold for classical real-time PCR using 1 μl potato extract was 3000 cfu/ml ($C_t$ value of 38.37; Table 3). In contrast, similar samples containing as few as 300 cfu's were positive ($C_t$ value of 36.38) with BIO-PCR. When the amount of sample used in the BIO-PCR reaction mixture was increased to 10 μl, the sensitivity increased to as few as 30 cfu's ($C_t$ value of 36.03; Table 3). In contrast, with a 10 μl sample and BIO-PCR, there was no significant difference between boiling and non-boiling. Typical $C_t$ values for boiling and non-boiling were 36.03 and 36.09, respectively, for plate washes containing 10 cfu.

Example 7

Assays of Naturally Infected Potato Tubers

A total of 14 tubers asymptomatic cv. Nordchip tubers were tested. The stem end core of each tuber was removed and added to 25 ml of buffer and 199 healthy tubers. After shaking for 4 h, the suspension was centrifuged and zero, $10^{-1}$, and $10^{-2}$ dilutions plated onto mSMSA agar, as above. As a control, 200 of the tubers purchased at a local grocery store were assayed similarly. Real-time direct and BIO-PCR was carried out as above.

BIO-PCR detected *R. solanacearum* in 2 out of 14 tubers. The extract of the two tubers resulted in $C_t$ values of 31.57 and 30.99, respectively. The same two tubers were positive by isolation techniques, also. Concentrations of *R. solanacearum* for the same two samples were 2000 and 3600 cfu/ml, respectively (Table 4). Direct real-time PCR detected *R. solanacearum* in the tuber containing 3600 cfu/ml ($C_t$ value of 38.3), but not in the one containing 2000 cfu/ml (Table 4). All assays were negative for the remaining, 12 tubers.

TABLE 4

Comparison between direct and BIO-PCR using real-time Smart Cycler for detecting Ralstonia solanacearum in 14 asymptomatic tubers.

| Tuber Number | No. of Colonies R. solanacearum[b] | Direct PCR[c] | BIO-PCR[d] |
|---|---|---|---|
| 1 | | | |
| Direct extract[a] | 200 | — | 31.7 |
| 1/10 dilution | 20 | — | 33.8 |
| 1/100 dilution | 2.0 | — | 37.3 |
| 2 | | | |
| Direct extract[a] | 360 | 38.3 | 31.0 |
| 1/10 dilution | 36 | — | 33.1 |
| 1/100 dilution | 3.6 | — | 36.5 |
| 3–14 | — | — | — |

[a]Potato tubers without any disease symptoms were extracted and the extract diluted to $10^{-1}$ and 100 μl plated onto each of five mSMSA plates. Three were incubated for visual counts of cfu's after 5 days and two washed for BIO-PCR after 24 h;
[b]Mean number of colonies per plate after three days at 28° C.;
[c]Results recorded as $C_t$ values: — equals no amplification. The water control was negative; $C_t$ value of a pure culture of *R. solanacearum*, positive control, was 22.5.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An oligonucleotide primer set consisting of a pair of oligonucleotide primers, one primer consisting of an eighteen to twenty-four nucleotide contiguous portion of SEQ ID NO:1 or of its full complement wherein said eighteen to twenty-four nucleotides of said primer comprises the contiguous sixteen nucleotide sequence 5'-TTCACCGCAAA-CAGCG-3' (SEQ ID NO:2), the second primer consisting of an eighteen to twenty-four nucleotide contiguous portion of SEQ ID NO:1 or of its full complement, wherein said eighteen to twenty-four nucleotides of said second primer comprises the contiguous sixteen nucleotide sequence 5'-TACGCCCCAGCAGATG-3' (SEQ ID NO:3), and wherein said primers of said primer set specifically hybridize to a region of SEQ ID NO:1 or its full complement, and wherein said primers thereby identify *Ralstonia solanacearum* biovar 2.

2. A probe comprising a detectable label conjugated to a fifteen to thirty nucleotide contiguous portion of SEQ ID NO:1 or of its full complement, wherein said fifteen to thirty nucleotides of said probe comprises the contiguous seventeen nucleotide sequence 5'-TTCGCCGATGCTTCCCA-3' (SEQ ID NO:4).

3. The probe of claim 2 wherein the detectable label is a chromophore or a fluorophore label.

4. A kit for detecting the presence of *R. solanacearum* biovar 2 comprising the probe of claims 2–3.

5. A method of detecting the presence of *Ralstonia solanacearum* biovar 2 by polymerase chain reaction, said method comprising:
   a) providing the DNA of *R. solanacearum* or a test sample suspected of containing the DNA of said *R. solanacearum*;
   b) amplifying a target sequence of DNA of said *R. solanacearum* using an oligonucleotide primer set consisting of a pair of oligonucleotide primers, one primer consisting of an eighteen to twenty-four nucleotide contiguous portion of SEQ ID NO:1 or of its full complement, wherein said eighteen to twenty-four nucleotides of said primer comprises the contiguous sixteen nucleotide sequence 5'-TTCACCGCAAA-CAGCG-3' (SEQ ID NO:2), the second primer consisting of an eighteen to twenty-four nucleotide contiguous portion of SEQ ID NO:1 or of its full complement, wherein said eighteen to twenty-four nucleotides of said second primer comprises the contiguous sixteen nucleotide sequence 5'-TACGC-CCCAGCAGATG3' (SEQ ID NO:3), and wherein said primers of said primer set specifically hybridize to a region of SEQ ID NO:1 or its full complement and are capable of identifying *R. solanacearum* biovar 2; and c) detecting the presence of amplification products of the target sequence of DNA as an indication of the presence of *R. solanacearum* biovar 2.

6. The method of claim 5, wherein amplification takes place under real-time PCR conditions and the amplification products are detected and quantitated by real-time analysis.

* * * * *